(12) United States Patent
Larsen

(10) Patent No.: US 6,605,067 B1
(45) Date of Patent: Aug. 12, 2003

(54) INJECTION NEEDLE

(75) Inventor: André Larsen, Drager (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 09/442,519

(22) Filed: Nov. 18, 1999

Related U.S. Application Data
(60) Provisional application No. 60/110,101, filed on Nov. 25, 1998.

(30) Foreign Application Priority Data

Nov. 20, 1998 (DK) .......................................... 1998 01524

(51) Int. Cl.[7] ................................................. A61M 5/32
(52) U.S. Cl. ...................................................... 604/192
(58) Field of Search ................................ 604/192, 187, 604/199, 195, 200, 214, 215, 236, 264, 265, 412, 413

(56) References Cited

U.S. PATENT DOCUMENTS

| | | | | |
|---|---|---|---|---|
| 4,058,121 A | * | 11/1977 | Choksi et al. ............... | 128/221 |
| 5,033,476 A | * | 7/1991 | Kasai ........................... | 128/764 |
| 5,569,210 A | * | 10/1996 | Moen .......................... | 604/191 |
| 5,910,133 A | * | 6/1999 | Gould ......................... | 604/164 |
| 5,935,113 A | * | 8/1999 | Dysarz ........................ | 604/263 |
| 6,102,894 A | * | 8/2000 | Dysarz ........................ | 604/110 |
| 6,146,594 A | * | 11/2000 | De Graaff et al. .......... | 422/100 |
| 6,235,003 B1 | * | 5/2001 | Dysarz ........................ | 604/195 |

FOREIGN PATENT DOCUMENTS

| | | |
|---|---|---|
| WO | WO 97/39787 | 10/1997 |
| WO | WO 99/25400 | 5/1999 |

OTHER PUBLICATIONS

Abstract of Japanese Patent JP 5096004 A.
Abstract of Japanese Patent JP 5096005 A.
Abstract of Japanese Patent JP 5096006 A.

* cited by examiner

*Primary Examiner*—Brian L. Casler
*Assistant Examiner*—Ann Y. Lam
(74) *Attorney, Agent, or Firm*—Marc A. Began; Richard W. Bork; Reza Green

(57) ABSTRACT

An injection needle unit for use on a syringe by patient administrated injections, comprising a hub fitting on the syringe which hub carries a needle having a cross section diameter less than 0,320, the needle being made from a super elastic material defined as a material which can obtain recovered elongation of more than 2% without having permanent deformation in the material. The injection needle can be forced away from its original linear shape and the force by which it seeks to return to this linear shape is used for automatic insertion of the needle.

20 Claims, 3 Drawing Sheets

INJECTION NEEDLE

CROSS-REFERENCE TO RELATED APPLICATIONS

This application claims priority under 35 U.S.C. 119 of U.S. provisional application No. 60/110,101 filed on Nov. 25, 1998, and Danish application no. PA 1998 01524 filed on Nov. 20, 1998, the contents of which are fully incorporated herein by reference.

BACKGROUND OF THE INVENTION

The invention relates to injection needle units for use on a syringe during patient administered injections. Such needle units comprise a hub fitting on a syringe and a needle mounted in the hub with pointed ends projecting from each end of the hub, i.e., a first end designed for penetrating the seal of a cartridge in a syringe and a second end designed for insertion into the skin of a patient to inject medicine from said cartridge.

Insofar as may people have needle phobia, which makes them reluctant to inject themselves, attempts have been made to develop needles which do not cause pain which can amplify this needle phobia.

Less pain by needle insertion is obtained by making the needles thinner and shorter. Whereas a lower limit for the length of the needles is set by the fact that an injection needle must be long enough to penetrate the skin and to deliver the medication subcutaneously, the limit for the thickness of the needle is set by the fact that a medicine shall be able to flow through the needle within an acceptable time and that the needle shall possess a mechanical strength so that it does not break or collapse when it is influenced by bending forces during the insertion and injection.

As it appears to be possible to make an insulin suspension and consequently other medicament solutions flow through needles as thin as G30 and even thinner, i.e. needles having outer diameters less than 0.320 mm and an inner diameter preferably larger than 0.13 mm, the mechanical strength sets the crucial limit for the thickness of a useable injection needle. Consequently, standards have been adopted which specify how much stainless steel injection needles for medical use are allowed to bend when influenced by defined forces.

SUMMARY OF THE INVENTION

It is an object of the invention to provided a needle having an outer diameter thinner than 0.320 mm which will not be in danger of breaking even when the limit sey by ISO 9626 are exceeded.

This is obtained by an injection needle unit for use on a syringe by patient administrated injections comprising a hub fitting on a syringe which hub carries a needle having a cross section diameter less than 0,320 mm and being mounted in the hub with pointed ends projecting from each end of the hub a first end designed for penetrating the seal of a cartridge in a syringe and a second end designed for insertion into the skin of a patient to inject medicine from said cartridge, wherein the needle according to the invention is made from an super elastic material which can obtain recovered elongation of more than 2% without having permanent deformation in the material. This elastic deformation can also be defined through Hooke's law $\sigma = E \times \epsilon$, where $\sigma$ is the strain, E is the Elasticity Modulus (Young's Modulus or Secant Modulus) and $\epsilon$ is the elongation. $\sigma$ and $\epsilon$ will be proportional with constant E-modulus when having a fully elastic deformation phase.

Such a super elastic behavior will e.g., be beneficial during repetitive bending of the needle to angles exceeding the limits defined in ISO 9626. Needles made from such super elastic material can be bent at rather sharp angles without breaking or collapsing and will, after having been bent, return to their linear shape.

According to the invention the needle may be made from a super elastic material from a special group of materials which in a given temperature interval change their crystal structure.

According to the invention the super elastic material used may be a NiTi alloy.

The use of super elastic needles for syringes is known from Japanese patent application No. 5-96004, which concerns injectors for analytical purposes designated as micro syringes. Such syringes are used to accurately measure small volumes of samples for injection into measuring instruments, some of which are capable of measuring a volume on the order of 0.1 microliters.

The high form stability and stiffness of an NiTi alloy containing 50.2 to 52.0 at. % Ni is taken advantage of in a needle with a diameter of 0.5 mm which maintains its linear shape when the needle is inserted into a needle guide of the injection device on sample injection into the measuring instrument. It is important that the needle maintains its linear shape as the piston can be moved into the lumen of the needle.

In needles for subcutaneous injections it is important that the needle is thin. Needles thinner than 0.320 mm are aimed at whereas it is less important if the needle is bent during the insertion if only it can be ensured that the needle do not break or collapse. This makes it attractive to use an alloy with a higher Ni content as needles made from such an alloy are less stiff but very elastic so that large deformations can be tolerated without any risk for breakage.

According to the invention an alloy containing at least 52% Ni and consisting of the balance Ti and unavoidable impurities is found appropriate.

The properties, inbreakability and elasticity, of the needle may be further enhanced by adding at least one further element at a content not higher than 4%.

In excess of being practically unbreakable the NiTi needle in spite of its large Ni content has shown to have a better biocompatibility than has ordinary stainless steel for medical purposes. Further the torsion strength and the ultimate strength of a NiTi needle is appreciably higher than for a corresponding needle made from conventional stainless steel.

Alternatively the needle may according to the invention be made from a curable or thermoplastic polymer super elastic material.

The needle hub may be of the kind comprising a sleeve with an internal thread, which sleeve forms the attachment means and can be screwed onto an outer thread on an attachment part of a syringe, and which hub has a base carrying the sleeve and the needle. The needle is fixed in the base with an injection part projecting from one side of said base and a back needle projecting from the other side of the base, the back needle being surrounded by the sleeve which projects from the base perpendicularly to said base on the same side as the back needle. When the hub is screwed onto a pen, the back needle may penetrate a rubber membrane which closes an ampoule in the pen. A medicine, e.g., insulin, can now be administered from the ampoule through the needle.

In an embodiment of the needle hub a needle guide may be provided which needle guide has an abutment surface by which it can abut the skin where the injection is going to be made, and a needle guide channel opening through said abutment surface. The needle which is movable relative to the abutment surface can be moved through the needle guide to make a sharpened end of the needle project from said surface. When the surface abuts the skin the needle will project through the skin into the underlying tissue. The needle guide may hide the needle to the user and the abutment of the abutment surface may distract the user so that he hardly feels the sting when the needle is inserted.

A small cavity may be provided in the abutment surface around the opening of the needle guide which may fit to the outer diameter of the needle so that air but hardly liquid can pass between the needle and the guide. The opening may be covered by a transparent cover plate which is frosted on its side facing the cavity. Before insertion of the needle its sharp end is positioned in the cavity beneath the cover plate. When a hub with a needle guide and with the above mentioned cavity covered with a frosted cover plate is mounted on a syringe it may be used as an air shot indicator. Air shots are made to ensure that air is driven out of the ampoule and the needle before attempt are made to inject medicine. To make an air shot a small dose is set and is pressed out through the needle the syringe being held with the injection part of the needle pointing vertically upward. This process is repeated until a thin jet of liquid is seen to leave the sharp end of the needle. When a needle with an air shot indicator of the above mentioned kind is used, air from the needle will pass away through the narrow gap between needle and needle guide. When liquid leaves the sharp end of the needle the cavity will quickly be filled and wet and the frosted surface which will then change appearance to be more clear. When the needle is going to be inserted through the skin it is passed through the cover plate and into the skin.

In another embodiment, the cavity in which the sharp end of the needle is positioned and which is covered by a cover plate may contain a lubricant that allows the needle to penetrate the skin more easily, or the cavity may contain an anesthetic to make the needle insertion totally painless.

In still another embodiment, the elasticity of the needle may be taken advantage of by providing an enforced curved course of the injection part of the needle between the base of the needle hub and the needle guide. With the enforced curved course, the sharp point of the injection part is positioned immediately beneath the abutment surface which is held against the skin. When the needle is going to be inserted, the enforcement is released and the needle will due to its elasticity straighten itself and thereby move the sharp end through the skin. If the needle itself does not possess the force needed for the straightening and insertion of the needle, the straightening may be assisted by a conventional spring element.

To ensure that the super elastic back needle do not deflect when the needle hub is mounted on a syringe where the super elastic needle shall penetrate the rubber membrane sealing a cartridge in the syringe a reinforcement of the back needle may be provided.

The reinforcement of the back needle may comprise a plastic needle integral with the needle hub surrounding the back needle of the super elastic needle injection needle or it may be a conventional stainless steel needle mounted in the needle hub in continuation of the super elastic needle or surrounding the back needle of said needle.

An embodiment of a needle unit may, according to the invention, comprise a needle hub comprising a base having a first and a second side. A sleeve projects from the first side of the base and forms attachment means by which the needle unit can be mounted onto an attachment part of a syringe. A housing projects from the second side of the base, in which housing a plug is axially displaceable. A needle is fixed in the base with a part forming a back needle projecting from the first side of the base and being surrounded by the sleeve. The rest of the needle projects from the second side of the base and is surrounded by the housing. Further, the needle is fixed in the plug with an injection part projecting from a distal end of the plug and an intermediary part running between a proximal end of the plug and the second side of the base.

When the plug is moved into the housing, the needle is forced to bend out from its linear shape. If the plug is released the needle will seek to return to its linear form whereby the plug and the injection needle part is moved in a distal direction. When the needle unit is held with its distal end against the skin where an injection is wanted, said movement in the distal direction will make the injection needle penetrate the skin and be ready for an injection of a medicine through the needle.

To avoid sharp bending of the intermediary needle at the transitions between this needle and the base and between this needle and the plug, respectively, flared recesses may be provided around the needle in said base and said plug at said transitions. These flared recesses will guide the needle to attain a curved shape without sharp bending when it is bent away from its linear shape. A similar guiding, flared recess may appropriately be provided at the transition between the plug and the injection needle.

BRIEF DESCRIPTION OF THE DRAWINGS

In the following the invention will be described in further details with references to the drawing, wherein.

DETAILED DESCRIPTION OF THE DRAWINGS

Figure 1:
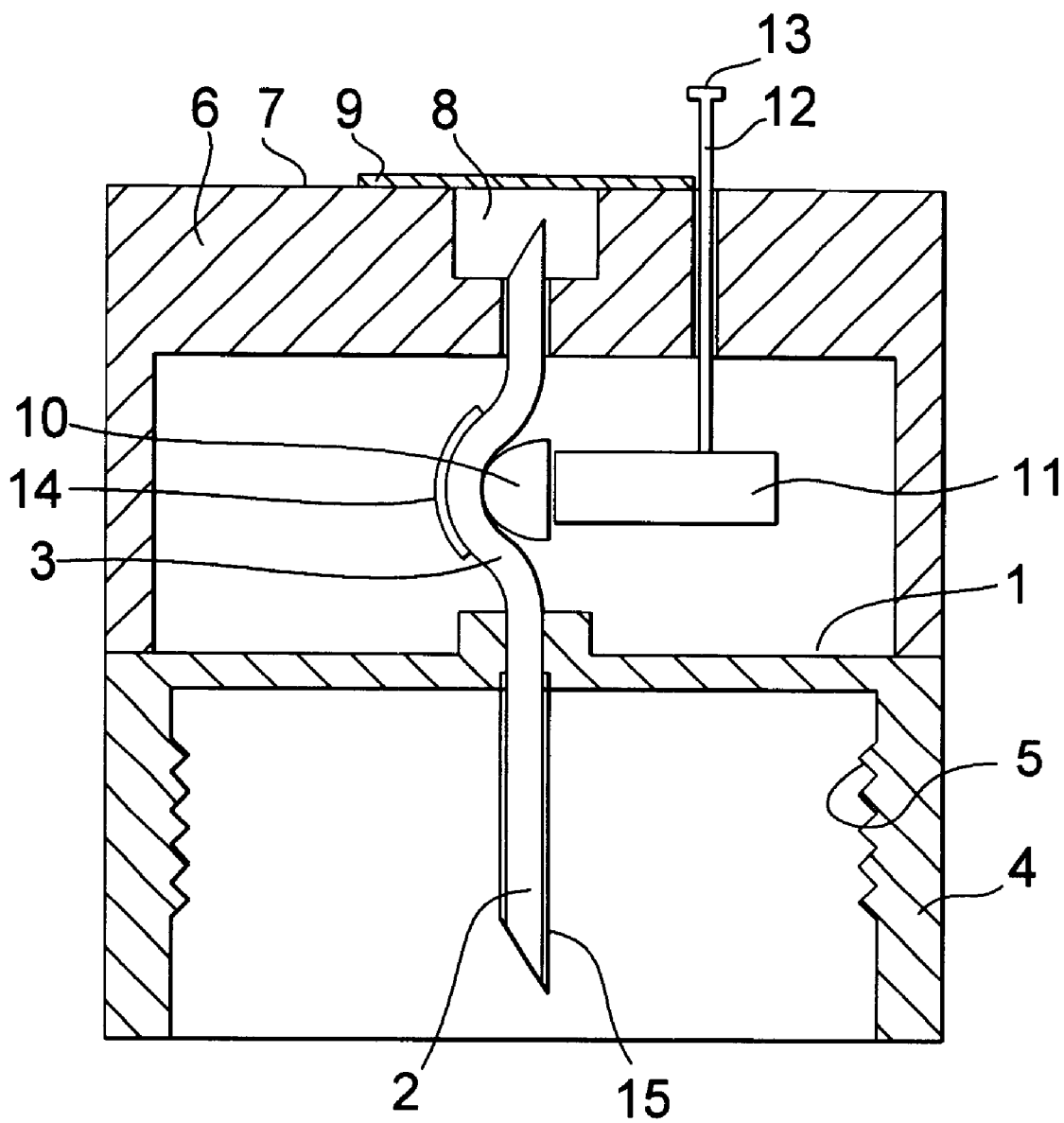
FIG. 1 shows a sectional view of a needle hub according to the invention.

As in a conventional needle hub the needle hub with the needle according to the invention comprises a needle, a base 1 through which the needle extends centrally forming a back needle 2 projecting from one side of the base 1 and a front needle 3 projecting from the other side of the base, the needle being fixed in the base either by a glue or by being embedded in the plastic material of the base, and a sleeve 4 depending from the perimeter of the base at the same side of this base as projects the back needle 2 which the sleeve surrounds concentrically. On its inner wall the sleeve is provided with a thread 5 by which the hub can be screwed onto a not shown injection syringe so that the back needle 2 pieces a closure of an ampoule in said syringe.

The needle is made from a super elastic alloy and can consequently be bent in rather sharp curves as shown in the drawing without collapsing or breaking and will try to return to its original straight shape when the bending forces are removed. Such alloys are mainly NiTi alloys.

Relative to a conventional needle hub the hub shown in the drawing has an attachment with a bottom plate 6 through which the front needle 3 can pass with a very small play so that this bottom acts as a guide for the front needle 3 when said front needle is inserted through the skin. The bottom plate has an abutment surface 7 which is placed in contact with the skin where the injection is intended to take place and when the sharp tip of the front needle is passed through the bottom plate this tip is guided into the skin as the small play between needle and bottom plate does not allow the needle to bend out.

A cavity 8 is provided in the abutment surface around the tip of the needle and the cavity is covered by a cover plate 9. When the attachment is a closed construction the cover plate 9 will act as a closure which ensures that the front needle can be kept in a sterile environment. The cavity 8 can be filled with a lubricant which makes the needle easy pass through the skin and/or an anaesthetic which makes the pain caused by the piercing not felt.

Alternatively the cover plate can have a frosted surface facing the cavity. As long as the cavity is filled with air the cavity will be seen as a dim spot on the cover plate 9. When so-called air shots are made to make the syringe ready for injection, which is done by setting a dose and pressing the injection button of the syringe without inserting the needle trough the skin, the spot over the cavity will remain dim as long as only air is injected in the cavity. As soon as liquid and not air is pressed out through the needle the cavity 8 will quickly fill this cavity and make the frosted surface clear to indicate that the syringe is ready for injection. The cover plate can be removable or can simply be pierced by the needle when this needle is moved out through the bottom plate 6 and into the tissue of the patient.

The insertion of the needle can be obtained by using a needle having a length making the needle, when straight, project from the bottom plate 6 a distance corresponding to a conventional needle length, e.g., about 6 mm. A half circular curve is induced in the front needle 3 between the hub base 1 and the needle guiding bottom plate 6 so that the tip of the needle is positioned behind the surface 7 in the cavity 8. The needle is kept in this position by releasable means, here illustrated as a block 10. The block 10 is held in position by a support 11 provided with at least one pin 12 which runs through the bottom plate 6. At a distance spaced from the abutment surface 7 of said bottom plate 6, the pin 12 is provided with a pad 13. When the abutment surface 7 is pressed against the skin, the pad 13 will first hit the skin and be pressed into the hub and the support 11 will be pressed away from the block 10 which will then be passed away by the needle which will, due to its inherent spring force, return to its straight shape. The needle will now project from the abutment surface 7 and into the skin of the patient. If the spring force of the needle is not sufficient to insert the needle, this force can be enhanced by using a stronger conventional spring, here shown as a leaf spring 14 attached to the curved part of the needle.

A common problem of thin needles is that the back needle is not sufficiently rigid to penetrate the sealing membrane of an ampoule without crumbling. To overcome this problem, the back needle may be reinforced by a conventional steel needle 15 or by a plastic sheath which is integral with the base material and forms part of the embedding of the needle in the base.

The curved part of the needle can have any appropriate curved shape and is not restricted to the half circular shape described, and also the release mechanism allowing the needle to regain its straight shape can be provided in any appropriate way without deviating from the scope of the invention.

Figure 2:
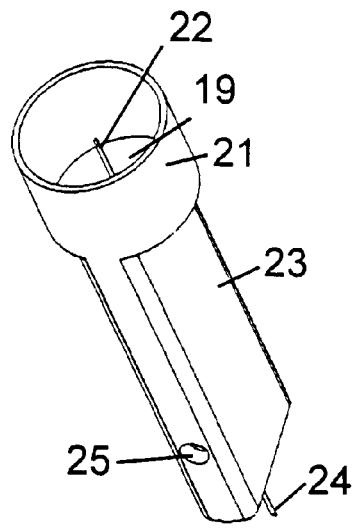
FIG. 2 shows a perspective view of another embodiment of a needle hub according to the invention.

FIG. 2 shows a perspective view of another embodiment of a needle with an automatic needle insertion mechanism. A sleeve 21 is provided with a not shown internal thread and can be screwed onto a socket on a cartridge. By this mounting, a back needle 22 penetrates a seal of a cartridge in the syringe. The back needle is a part of a needle which is fixed in a bottom 19 in the sleeve and runs all the way through a housing 23 to project from the opposite end of this housing as an injection needle 24.

Figure 3:
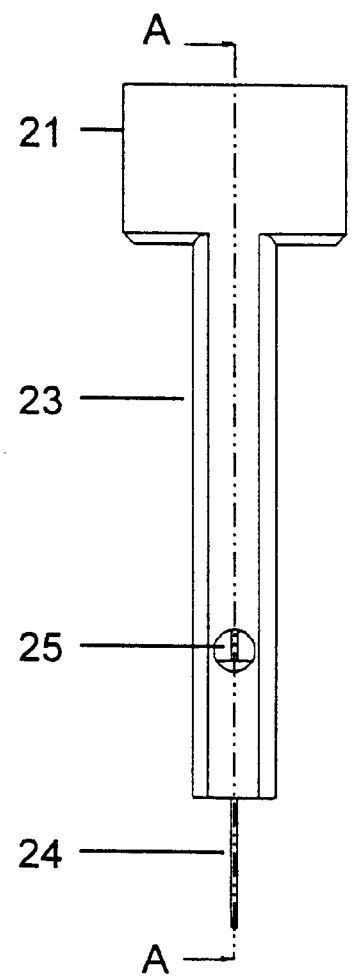
FIG. 3 shows a side view of the needle hub in FIG. 2.
Figure 4:
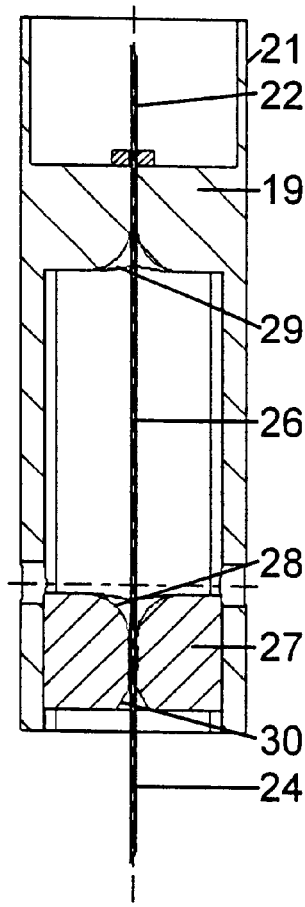
FIG. 4 shows a sectional view along the line 4—4 in the needle hub in FIG. 3.

FIG. 3 shows a side view of the needle unit of FIG. 2 and FIG. 4 shows a sectional side view of the needle in FIG. 3 rotated 90° about its longitudinal axis. The needle 26 which connects the back needle 22 and the injection needle 24 and is integral with said back needle 22 and injection needle 24 is at its proximal end fixed in the end wall 19 which is integral with the housing 23 and at its distal end fixed in a plug 27 which is displaceable in the longitudinal direction of the housing.

Figure 5:
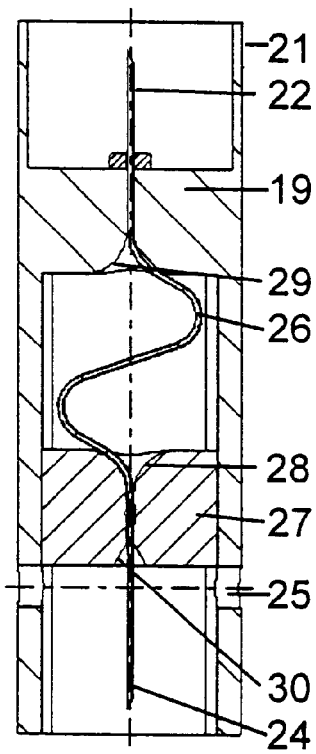
FIG. 5 shows the needle hub in FIG. 4 cocked for automatic needle insertion.

As shown in FIG. 5, the plug 27 may be forced into the housing whereby the needle 26 is given a curved course through the housing 23. At the transitions between the needle 26 and the plug 27 and the needle 26 and the bottom 19, respectively, flared conical recesses 28 and 29, respectively, are formed whereby the needle 26 is guided so that it is not bent at a sharp angle at these transitions. A similar flared conical recess 30 is made around the injection needle to avoid sharp bending at the transition between the plug 27 and this injection needle 24. When the plug 27 is pressed into the housing 23, the needle is forced to the position shown in FIG. 5 and the elasticity of the needle 26 will seek to return it to its linear appearance and will press the plug 27 in the distal direction. Movement of the plug 27 may be blocked by the insertion of a not shown pin under the plug 27 through an opening 25 in the housing 23 so that the plug is held in a position in which the whole injection needle 24 is hidden in the housing. The distal end of the housing may now be pressed against the skin where an injection is wanted and when the not shown pin is removed from the opening 25 the needle 26 will, due to its elasticity, return to its linear shape and press the plug in the distal direction and thereby press the injection needle 24 through the skin ready for an injection.

Figure 6:
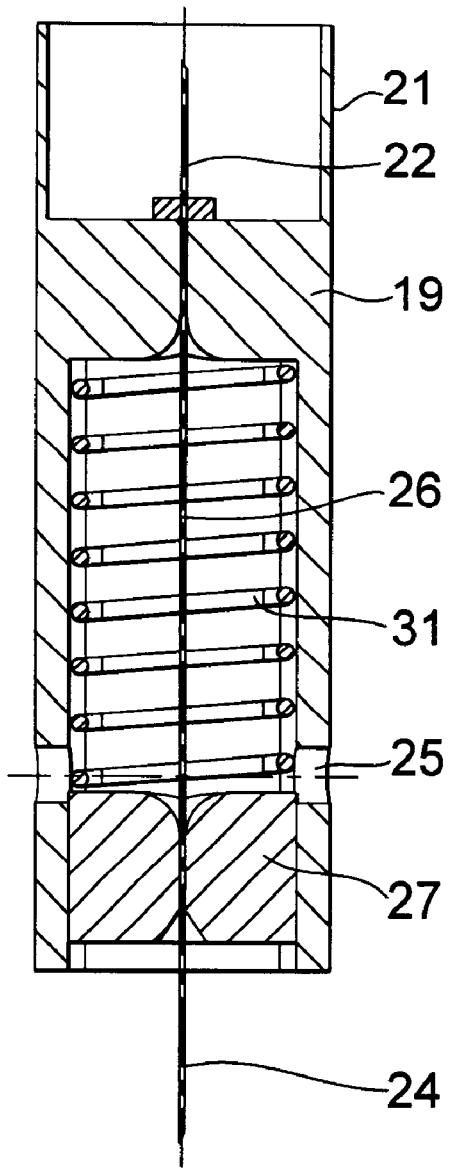
FIG. 6 shows the needle hub in FIG. 4 wherein the a helical spring provides some of the needle insertion force.
Figure 7:
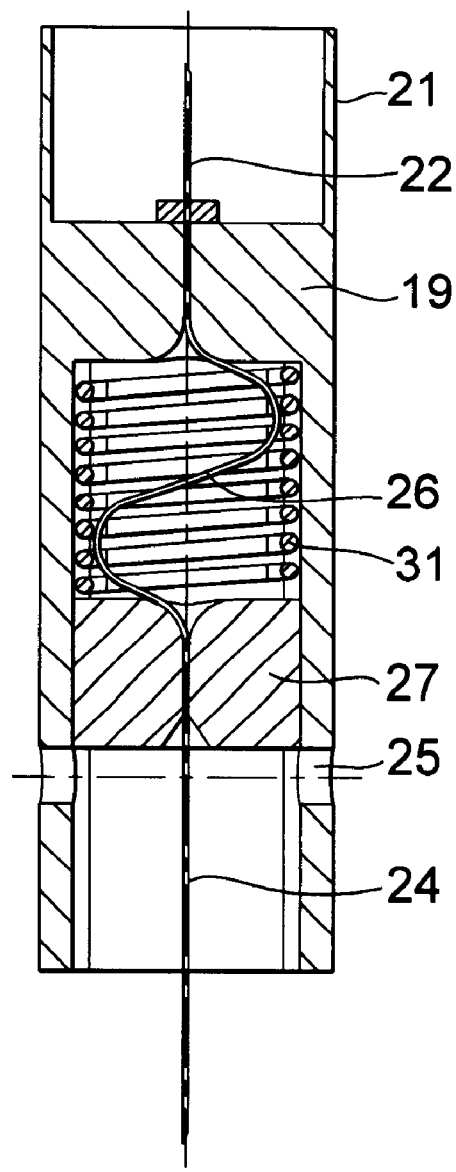
FIG. 7 shows the needle hub in FIG. 6 cocked for automatic needle insertion.

If the elasticity of the needle 26 is not sufficient to provide the force necessary to insert the injection needle 24 through the skin the force provided by the needle itself it can be supplemented by a conventional helical spring 31 as shown in FIGS. 6 and 7 which shows sectional views corresponding to FIG. 4 and 5.

What is claimed is:

1. An injection needle unit for use on a syringe during patient administrated injections, comprising a hub for fitting the unit on the syringe which hub carries a needle having a cross section diameter less than 0.320 mm and being mounted in the hub with pointed ends projecting from each end of the hub including a first end designed for penetrating the seal of a cartridge in a syringe and a second end designed for insertion into the skin of a patient to inject medicine from said cartridge, wherein the needle is made from a super elastic material defined as a material which can obtain recovered elongation of more than 2% without having permanent deformation in the material.

2. An injection needle unit according to claim 1, wherein the needle is made from a super elastic material which belongs to a special group of materials which in a given temperature interval change their crystal structure.

3. An injection needle unit according to claim 2, wherein the super elastic material used is a NiTi alloy.

4. An injection needle unit according to claim 3, wherein the NiTi alloy contains at least 52% Ni and consists of the balance Ti and unavoidable impurities.

5. An injection needle unit according to claim 3, wherein the NiTi alloy contains at least one further element at a content not higher than 4%.

6. An injection needle unit according to claim 1 wherein the needle is made from a curable or a thermoplastic material.

7. An injection needle unit according to claim 1, wherein the needle hub comprises a base and a sleeve with an internal thread, which sleeve forms attachment means and can be screwed onto an outer thread on an attachment part of a syringe, and wherein the needle is fixed in the base with an injection part projecting from one side of said base and a back needle projecting from the other side of the base, the back needle being surrounded by the sleeve which depends from the perimeter of the base perpendicularly to said base on the same side as the back needle.

8. An injection needle unit according to claim 1, wherein the hub has a needle guide comprising an abutment surface for abutment with the skin where the injection is going to be made, and a needle guide channel opening through said abutment surface through which needle guide channel the needle is movable relative to the abutment surface to make a sharpened end of the needle project from said surface.

9. An injection needle unit according to claim 8, wherein a cavity is provided in the abutment surface around the opening of the needle guide channel which cavity is covered by a cover plate sealed to the abutment surface.

10. An injection needle unit according to claim 9, wherein a surface of the cover plate facing the cavity is frosted.

11. An injection needle unit according to claim 9, wherein the cavity is filled with a lubricant.

12. An injection needle unit according to claim 9, wherein the cavity is filled with an anaesthetic.

13. An injection needle unit according to claim 8, wherein means are provided enforcing a curved course of the needle between the base of the needle hub and the needle guide so that the sharp point of the needle is positioned immediately beneath the abutment surface, and wherein release means are provided which removes said enforcement so that the needle due to its elasticity recovers a straight shape.

14. An injection needle unit according to claim 13, wherein a spring element is provided which assists the straightening of the needle.

15. An injection needle unit according to claim 14, wherein the spring element is a leaf spring adjacent to the curved part of the needle.

16. An injection needle unit according to claim 1, wherein a reinforcement of the first end is provided.

17. An injection needle unit according to claim 16, wherein the reinforcement of the first end comprises a plastic needle integral with the needle hub surrounding the back needle of the super elastic needle.

18. An injection needle unit according to claim 16, wherein the reinforcement of the first end is a conventional stainless steel needle mounted in the needle hub.

19. An injection needle unit according to claim 1, wherein said needle hub comprises a base having a first and a second side, a sleeve projecting from the first side of the base and forming attachment means by which it can be mounted onto an attachment part of a syringe, and a housing projecting from the second side of the base, a plug axially displaceable in said housing, wherein said needle is fixed in the base with a part forming a back needle projecting from the first side of the base and being surrounded by the sleeve, and the rest of the needle projecting from the second side of the base and being surrounded by the housing, the needle further being fixed in the plug with an injection part projecting from a distal end of the plug and an intermediary part running between a proximal end of the plug and the second side of the base.

20. An injection needle unit according to claim 19, wherein a guiding flared recess is provided around the needle at the transition between the plug and the intermediary part of the injection needle.

* * * * *